United States Patent
Pasquale et al.

(10) Patent No.: US 6,758,823 B2
(45) Date of Patent: Jul. 6, 2004

(54) ASSESSMENT OF RETINAL FUNCTION

(75) Inventors: Louis R. Pasquale, Newton Highlands, MA (US); Steven Brusie, Newton, MA (US)

(73) Assignee: Massachusetts Eye & Ear Infirmary, Boston, MA (US)

(*) Notice: Subject to any disclaimer, the term of this patent is extended or adjusted under 35 U.S.C. 154(b) by 168 days.

(21) Appl. No.: 10/072,453

(22) Filed: Feb. 8, 2002

(65) Prior Publication Data

US 2002/0133089 A1 Sep. 19, 2002

Related U.S. Application Data

(60) Provisional application No. 60/267,985, filed on Feb. 9, 2001.

(51) Int. Cl.[7] .............................................. A61B 13/00
(52) U.S. Cl. .................................................... 600/558
(58) Field of Search .................... 351/211, 214, 351/224, 226, 246; 600/558

(56) References Cited

U.S. PATENT DOCUMENTS

| | | | | | |
|---|---|---|---|---|---|
| 4,255,023 A | * | 3/1981 | House | ......................... | 351/226 |
| 4,846,567 A | * | 7/1989 | Sutter | ......................... | 351/224 |
| 5,640,220 A | | 6/1997 | Vo et al. | ..................... | 351/213 |

OTHER PUBLICATIONS

International Search Report date mailed Jul. 12, 2002.

* cited by examiner

*Primary Examiner*—George Manuel
(74) *Attorney, Agent, or Firm*—Fish & Richardson P.C.

(57) ABSTRACT

A method for assessing a patient's retinal function includes selecting a test site on a retina of the patient and stimulating the test site. In a healthy retina, this stimulation results in the generation of an entoptic signal, which is then detected. The method thus provides a simple test for detecting damage to retinal ganglion cells in glaucoma.

30 Claims, 3 Drawing Sheets

ASSESSMENT OF RETINAL FUNCTION

RELATED APPLICATIONS

This application claims the benefit of the Feb. 9, 2001 priority date of U.S. Provisional Application 60/267,985, the contents of which are herein incorporated by reference.

FIELD OF INVENTION

This invention relates to ophthalmologic methods and systems, and in particular, to methods and systems for detecting damage to the retina, such as that caused by glaucoma.

BACKGROUND

The retina is a highly organized but complex neurosensory tissue that processes visual information and transmits it to the brain along the optic nerve. The optic nerve, which connects the eye to the brain, is predominantly a bundle of axons, or fiber-like projections of neuronal cells called retinal ganglion cells. These retinal ganglion cell axons fan out along the superficial aspect of the retina in arcuate bundles. When light stimulates photoreceptors, which are located under these arcuate bundles, a signal is transmitted, via a complicated array of intervening neuronal cells, to the retinal ganglion cell body. The retinal ganglion cell axons then relay this signal through an exit site, referred to as the "optic nerve head", in the posterior wall of the eye. The optic nerve head corresponds functionally to the blind spot in vision because, at this location, there are no underlying photoreceptor cells.

Glaucoma is a disease of the retinal ganglion cell bodies and their axons. In a patient having glaucoma, the retinal ganglion cells slowly lose their ability to transmit nerve impulses. As a result, vision diminishes, often so slowly that a patient afflicted with this disease does not notice the degradation in vision until significant damage has occurred. It is in this insidious manner that glaucoma robs the patient of sight. When detected early enough, glaucoma can be managed. However, because glaucoma has few overt symptoms, it is difficult to detect early.

One approach to testing for glaucoma is to use a tonometer to measure intra-ocular pressure. This test is based on the notion that high intra-ocular pressure can damage the retinal ganglion layer. However, in practice, intra-ocular pressure has not proven to be a reliable indicator for glaucoma.

A more reliable test for glaucoma is a visual field test in which light is directed to various portions of the retina. By asking the patient whether he sees the light, one can map the sensitivity of the retina. Because the field vision test measures optic nerve function more directly, it is a more accurate indicator of glaucoma than the tonometric test. However, the visual field test is a time-consuming test that requires expensive equipment operated by trained personnel. Furthermore, the visual field test assesses all components of the visual system, from the tear film to the occipital cortex in the brain. It is not testing the function of retinal ganglion cells specifically. As a result, it can be difficult to distinguish pathology of retinal ganglion cells from pathologies of other components of the visual system.

SUMMARY

The invention is based on the recognition that under certain circumstances, a patient having normal retinal function will perceive an entoptic signal. This entoptic signal, which most commonly appears to the patient as a blue arc, is believed to originate in the retinal ganglion cell axons. A patient's inability to perceive this entoptic signal is correlated with the likelihood that the patient's retina has experienced damage, perhaps from early stages of glaucoma. This correlation is exploited in a simple and inexpensive test for evaluating the likelihood that a patient has glaucoma.

A method according to the invention includes selecting a test site on a retina of the patient and stimulating that test site to cause the generation of an entoptic signal. The entoptic signal need not be generated at the test site but can be generated sewhere in the eye. The entoptic signal generated as a result of the stimulus is then detected. In some practices of the invention, the entoptic signal is detected by accepting an input from the patient that indicates whether or not the patient has perceived any visual manifestation of the entoptic signal. In other practices of the invention, entoptic signal is detected by obtaining an objective measurement with a device for measurement of electromagnetic fields or waves.

In some practices of the invention, the test site is selected to be temporal, or peripheral to the patient's optic nerve head. In other practices of the invention, selecting a test site includes providing a target upon which the patient is to fixate. In those cases, stimulating the test site includes displaying, to the patient, a test figure peripheral to the target.

The test site can be stimulated by illuminating it with a test figure. Alternatively, the test site can be stimulated by displaying a test figure to the patient on, for example, a computer monitor or a specialized display device. In either case, the test figure can periodically be made to flash on and off. The frequency and duty cycle with which the test figure flashes is selected to enhance the patient's visual perception of the entoptic signal.

These and other features of the invention will be apparent from the following figures, in which:

DETAILED DESCRIPTION

Figure 1:
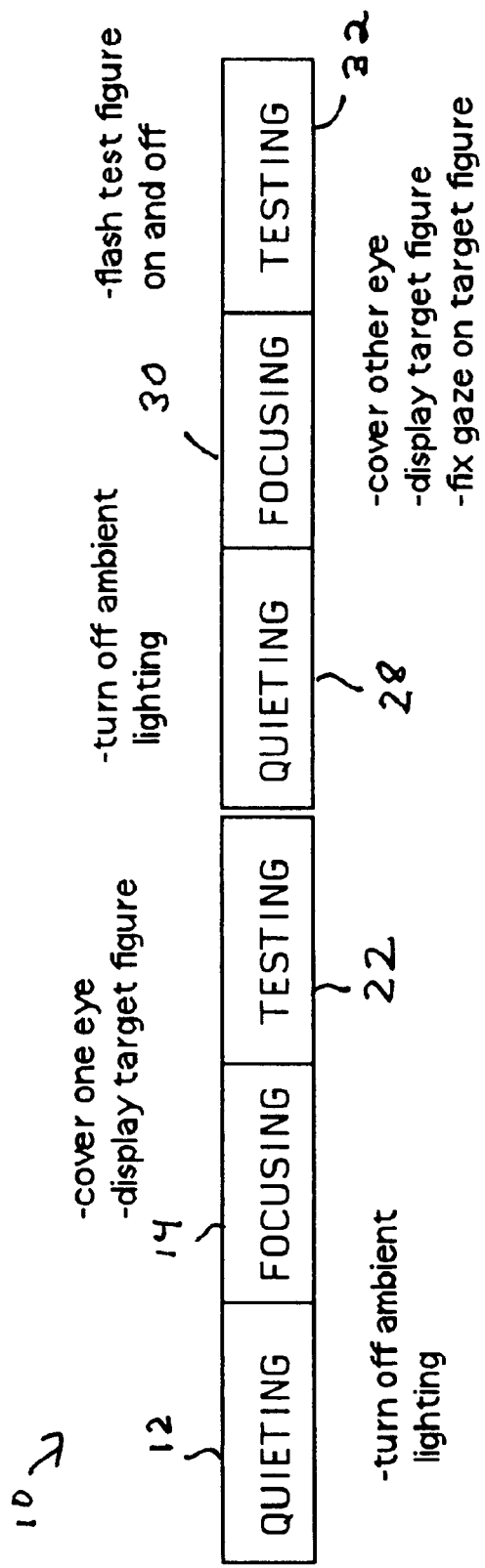
FIG. 1 is a time-line of a glaucoma diagnosis method.

Referring to FIG. 1, one practice of the glaucoma diagnosis method 10 begins with a first quieting interval 12 in which the patient is seated before a computer monitor, ambient lighting is turned off, and the patient closes both eyes. This allows any electrical activity within the patient's retinas to become as quiescent as possible. This first quieting interval typically lasts on the order of one or two minutes.

Figure 2:
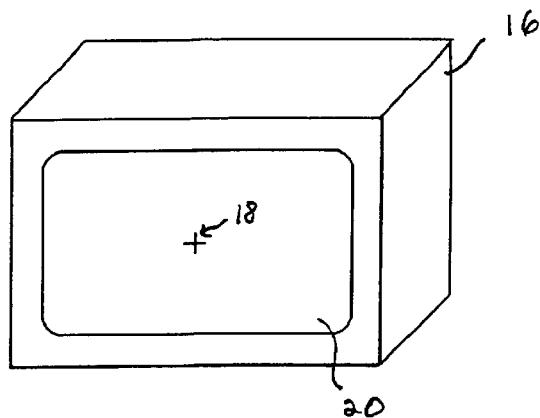
FIG. 2 shows a target figure.

Following the first quieting interval 12 is a first focusing interval 14 during which a computer monitor 16 displays a target figure 18, as shown in FIG. 2. The target figure is centered on a black background on the computer monitor's display area 20. With his left eye covered, the patient fixates on the target figure 18 with his right eye.

Figure 3:
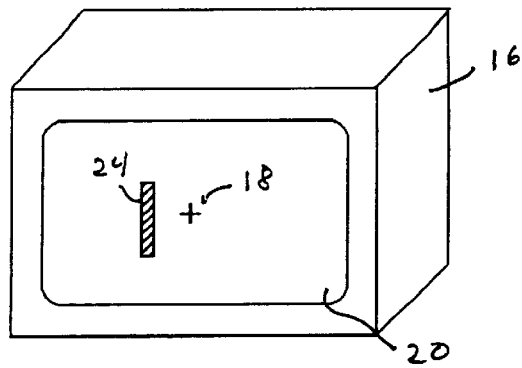
FIG. 3 shows a test figure next to the target figure of FIG. 2.

Immediately after the first quieting interval 12, a first testing interval 22, lasting approximately twenty-five seconds, begins. During this first testing interval 22, a test figure 24 is periodically displayed adjacent to the target figure 18, as shown in FIG. 3. The actual size, shape, color, luminance of the test figure 24, and its location relative to the target figure 18, can be varied in order to enhance the patient's perception of entoptic light. For example, in FIG. 3, the test figure 24 is positioned on the side of the target figure 18 that is toward the patient's nose e.g. the test figure 24 is located in the patient's nasal visual field and projects to a retinal location temporal to the fovea). Hence, the test figure 24 shown in FIG. 3 is as it would appear for testing the patient's right eye.

To the extent that the patient fixates on the target figure 18, the portion of the retina illuminated by the test figure 24 will lie temporal to the patient's fovea. The blind spot will lie on the side of the fovea opposite to the test figure, or nasal to the patient's fovea.

Figure 4:
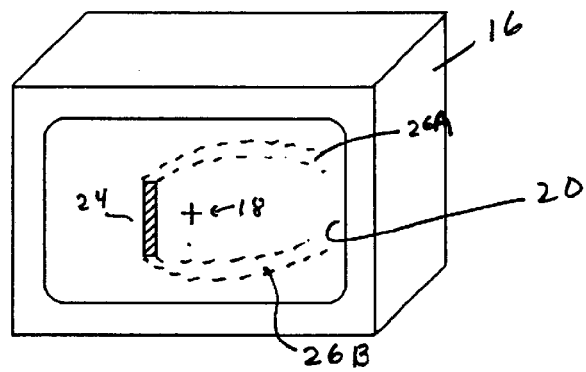
FIG. 4 shows the location of blue arcs perceived by the patient's right eye.

During the first testing interval 22, the test figure 24 is flashed on and off. As it does so, the patient is asked whether he perceives a pair of blue arcs 26A–B. In most cases, the blue arcs 26A–B will appear to extend away from the test figure 24 as shown in FIG. 4, arcing around the target figure and converging toward an invisible point on the opposite side of the display. These blue arcs 26A–B are not actually present on the display surface 20. Instead, the patient perceives these blue arcs 26A–B in response to the retinal stimuli provided during the first testing interval 22. A patient who fails to perceive the blue arcs 26A–B is considered to be more at risk of having glaucoma or other optic nerve disease than a patient who does perceive the blue arcs 26A–B.

In practice, the perceived shapes of the blue arcs 26A–B and their perceived color can vary from patient to patient. In addition, certain patterns of damage to the optic nerve, whether from glaucoma or other optic nerve diseases, can cause the patient to perceive only one blue arc.

Figure 5:
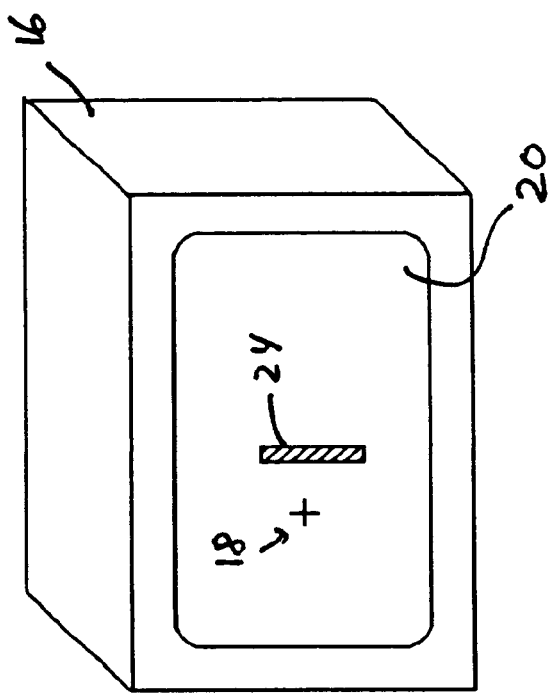
FIG. 5 shows the test figure on the other side of the target figure.

The first testing interval 22 is followed by a second quieting interval 28. This is followed by a second focusing interval 30 in which the patient covers his right eye and fixates on the target figure 18 with his left eye. During a second testing interval 32 that follows, the test figure 24 is displayed on the opposite side of the target figure 18 so that it stimulates an area of the retina temporal to the fovea of the left eye, as shown in FIG. 5.

Figure 6:
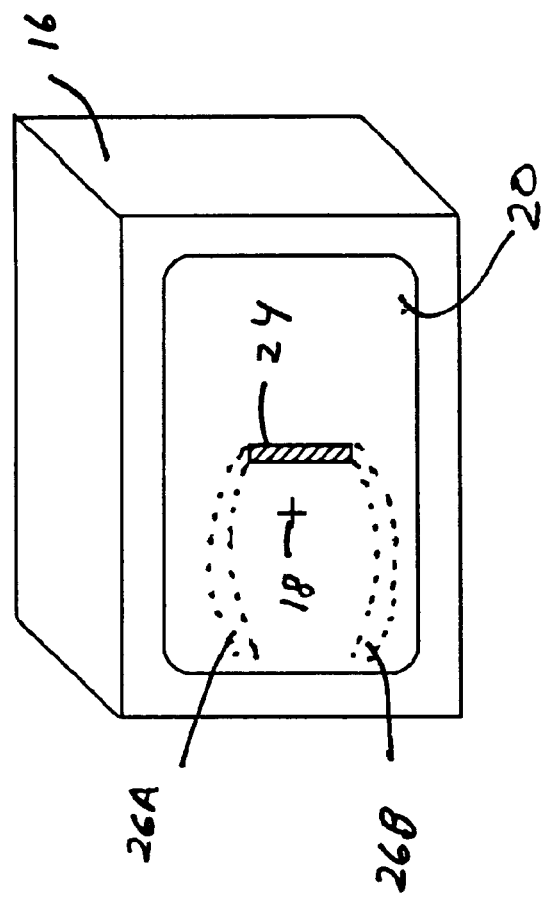
FIG. 6 shows the location of blue arcs perceived by the patient's left eye.

During the second testing interval 32, the test figure 24 is again flashed on and off. As it does so, the patient is again asked whether he perceives a pair of blue arcs 26A–B extending away from the test figure 24, arcing around the target figure 18 and converging toward an invisible point on the opposite side of the display, as shown in FIG. 6.

In one practice of the invention, the test figure 24 and the target figure 18 are displayed on a conventional computer display, such as a cathode ray tube or a flat panel display. Such displays are advantageous because of their widespread availability. However, conventional computer displays offer only limited luminance. Hence, in another practice of the invention, the target figure 18 and the test figure 24 can be displayed on a specialized high-luminance display.

In an alternative practice of the invention, the test figure 24 can be projected directly onto the retina using known optical projection systems. This practice is advantageous because it no longer relies on the patient's ability to remain fixated on the target figure 18 during the testing interval.

The target figure 18 can be an "x" or a small cross rendered in gray or white. Typically, the target figure 18 is small enough so that to avoid generating unnecessary electrical activity within the retinal ganglion cell axons but large enough to capture the patient's gaze. The appropriate angular extent can be achieved by controlling the image size on the display or by seating the patient at different distances from the display.

The test figure 24 can be any shape or color. However, it has been found experimentally that a red vertical bar enhances the patient's perception of the blue arc. The vertical extent of the test figure 24 is selected such that the vertical image on the retina is slightly longer than the macula. In particular, with the patient's eyes located 40 centimeters from the display, the test figure 24 subtends 5 degrees of arc above and below a horizontal line defined by the target figure 18. Along its minor axis, the test figure 24 subtends 0.86 degrees of arc. The test figure 24 is disposed approximately 2.3 degrees of arc nasal to the target figure 18.

It is also not necessary that the test figure 24 flash during the first and second testing intervals. However, it has been found that flashing the test figure 24 enhances the patient's perception of the blue arc. A preferred flashing sequence includes repeatedly displaying the test figure 24 for half a second and hiding it for two seconds.

A disadvantage of the foregoing practice lies in its reliance on a patient's subjective perception of the blue arcs 26A–B. To circumvent this, one practice of the invention includes a detector for detecting any electromagnetic fields or waves that cause the patient to perceive the blue arc. One example of such a detector is a photomultiplier, configured to detect any photons emitted by the retinal ganglion cell axon.

One implementation of the glaucoma test is in the form of a POWERPOINT (™) presentation. In this embodiment, the individual presentation slides can be sequentially displayed at a controlled rate. However, any software that can produce an animated display can be used to implement the glaucoma test of the invention.

Having described the invention, and one preferred embodiment thereof, what we claim as new and secured by Letters Patent is:

1. A method for assessing retinal function, said method comprising:
   selecting a test site on a retina of a patient;
   stimulating said test site to cause generation of an entoptic signal; and
   detecting said entoptic signal.

2. The method of claim 1 wherein selecting a test site comprises selecting a test site peripheral to the optic nerve head of said patient.

3. The method of claim 2, wherein selecting a test site comprises providing a target upon which said patient is to fixate and stimulating said test site comprises displaying, to said patient, a test figure peripheral to said target.

4. The method of claim 1, wherein stimulating said test site comprises illuminating said test site with a test figure.

5. The method of claim 4, wherein illuminating said test site comprises defining a test interval and periodically illuminating said test site with said test figure.

6. The method of claim 5, wherein periodically illuminating said test site comprises selecting a frequency of illumination to enhance said patient's perception of said entoptic signal.

7. The method of claim 4, wherein illuminating said test site comprises selecting said test figure to enhance said patient's perception of said entoptic signal.

8. The method of claim 1, wherein illuminating said test site comprises selecting an intensity of illumination to enhance said patient's perception of said entoptic signal.

9. The method of claim 1, wherein detecting said entoptic signal comprises receiving input from said patient, said input being indicative of said patient's perception of said entoptic signal.

10. The method of claim 1, wherein stimulating said test site comprises displaying a test figure to said patient.

11. The method of claim 10, wherein displaying a test figure comprises displaying said test figure on a computer monitor.

12. The method of claim 1, further comprising determining whether glaucoma is likely to be present on the basis of detection of said entoptic signal.

13. The method of claim 1, wherein said entoptic signal comprises a signal perceived as entoptic light.

14. The method of claim 1, wherein said entoptic signal comprises a signal perceived as a blue arc.

15. A system for assessing retinal function, said system comprising:
   a display element configured to display a test figure; and
   a display controller for controlling said display element so as to stimulate generation of an entoptic signal.

16. The system of claim 15, wherein said display element comprises a computer monitor.

17. The system of claim 15, wherein said display element comprises a projection system for projecting an image of said test figure directly onto a selected spot on said retina.

18. The system of claim 15, further comprising a detector for detecting an electromagnetic field indicative of said entoptic signal.

19. The system of claim 15, wherein said controller is a manual controller.

20. The system of claim 15, wherein said controller is an automatic controller.

21. A computer-readable medium having encoded thereon software for assessing retinal function, said software comprising instructions for:
   selecting a test site on a retina of a patient;
   stimulating said test site to cause generation of an entoptic signal; and
   detecting said entoptic signal.

22. The computer-readable medium of claim 21 wherein said instructions for selecting a test site comprise instructions for selecting a test site peripheral to an optic nerve head of said patient.

23. The computer-readable medium of claim 21, wherein said instructions for selecting a test site comprise instructions for providing a target upon which said patient is to fixate and said instructions for stimulating said test site comprise instructions for displaying, to said patient, a test figure peripheral to said target.

24. The computer-readable medium of claim 21, wherein said instructions for stimulating said test site comprise instructions for illuminating said test site with a test figure.

25. The computer-readable medium of claim 24, wherein said instructions for illuminating said test site comprise instructions for defining a test interval and periodically illuminating said test site with said test figure.

26. The computer-readable medium of claim 25, wherein said instructions for periodically illuminating said test site comprise instructions for selecting a frequency of illumination to enhance said patient's perception of said entoptic signal.

27. The computer-readable medium of claim 24, wherein said instructions for illuminating said test site comprise instructions for selecting said test figure to enhance said patient's perception of said entoptic signal.

28. The computer-readable medium of claim 21, wherein said instructions for illuminating said test site comprise instructions for selecting an intensity of illumination to enhance said patient's perception of said entoptic signal.

29. The computer-readable medium of claim 21, wherein said instructions for detecting entoptic light comprise instructions for receiving input from said patient, said input being indicative of said patient's perception of said entoptic signal.

30. The computer-readable medium of claim 21, wherein said instructions for stimulating said test site comprise instructions for displaying a test figure to said patient.

* * * * *